(12) United States Patent
Pollack

(10) Patent No.: US 11,628,040 B2
(45) Date of Patent: Apr. 18, 2023

(54) IDENTIFICATION BRACELET

(71) Applicant: David Pollack, Fort Lee, NJ (US)

(72) Inventor: David Pollack, Fort Lee, NJ (US)

( * ) Notice: Subject to any disclaimer, the term of this patent is extended or adjusted under 35 U.S.C. 154(b) by 0 days.

(21) Appl. No.: 17/064,666

(22) Filed: Oct. 7, 2020

(65) Prior Publication Data

US 2022/0104917 A1 Apr. 7, 2022

(51) Int. Cl.
*A61B 90/98* (2016.01)
*G09F 3/00* (2006.01)
*A44C 5/14* (2006.01)
*G09F 3/20* (2006.01)
*A61B 90/96* (2016.01)

(52) U.S. Cl.
CPC .............. *A61B 90/98* (2016.02); *A44C 5/145* (2013.01); *A61B 90/96* (2016.02); *G09F 3/005* (2013.01); *G09F 3/0297* (2013.01); *G09F 3/201* (2013.01)

(58) Field of Classification Search
CPC ....... G09F 3/005; A61B 90/90; A44C 5/0023; A44C 5/0015
See application file for complete search history.

(56) References Cited

U.S. PATENT DOCUMENTS

| | | | | |
|---|---|---|---|---|
| 4,906,025 A * | 3/1990 | Schreindl | ............... | B42D 5/006 224/267 |
| 10,791,805 B1 * | 10/2020 | Piccolella | ............ | A44C 5/0015 |
| 2003/0106336 A1 * | 6/2003 | Gaskill | ................ | A44C 5/0023 63/3 |
| 2005/0066563 A1 * | 3/2005 | Juhan | ...................... | G09F 3/005 40/633 |
| 2005/0091919 A1 * | 5/2005 | Weiner | .................... | A01G 9/00 47/66.6 |
| 2005/0242137 A1 * | 11/2005 | Fishman | .............. | A01K 27/006 224/221 |
| 2006/0261958 A1 * | 11/2006 | Klein | ................... | A01K 11/006 340/572.8 |
| 2009/0265971 A1 * | 10/2009 | Cook | ..................... | G09F 3/005 40/633 |
| 2010/0132237 A1 * | 6/2010 | McDermott | ......... | A44C 5/0015 40/633 |
| 2010/0242325 A1 * | 9/2010 | Waltersdorf | ............ | G09F 3/005 40/633 |
| 2011/0079045 A1 * | 4/2011 | Bielkiewicz | ............ | G09F 23/00 63/1.13 |

(Continued)

*Primary Examiner* — David R Dunn
*Assistant Examiner* — Christopher E Veraa
(74) *Attorney, Agent, or Firm* — Law Office of Ilya Libenzon

(57) ABSTRACT

An identification bracelet includes a wristband securable to a wearer. The wristband includes a plurality of openings for receiving a locking rivet and one or more openings for receiving one or more color-coded pins, a housing attached to the wristband, the housing having a pair of lugs with a slit, each lug extending from each side of the housing and adapted to receive the corresponding ends of the wristband inserted into the corresponding slits. The housing comprises a snap-on cover with at least a portion of the cover being transparent, a base, and a waterproof gasket insertable into the base. The snap-on cover is configured to be snapped on the base thereby creating a hermetically sealed waterproof structure. The housing also includes an information tag insertable into the housing and visible through the transparent portion of the housing.

21 Claims, 5 Drawing Sheets

(56) References Cited

U.S. PATENT DOCUMENTS

| | | | | |
|---|---|---|---|---|
| 2011/0226861 A1* | 9/2011 | Warther | ........... | G06K 19/07749 29/601 |
| 2011/0277501 A1* | 11/2011 | Davis | ................... | A44C 5/0053 63/1.13 |
| 2012/0234040 A1* | 9/2012 | Murphy | ............... | A44C 5/0015 63/1.11 |
| 2013/0074544 A1* | 3/2013 | Lans | ....................... | G09F 3/005 40/6 |
| 2016/0038241 A1* | 2/2016 | Dutt | ......................... | G09F 3/02 40/665 |
| 2018/0365548 A1* | 12/2018 | Karani | ............... | G06K 19/0715 |
| 2020/0184853 A1* | 6/2020 | Schmid | .................... | G09F 3/16 |
| 2020/0289001 A1* | 9/2020 | Mantrawadi | .............. | A45F 5/00 |

* cited by examiner

IDENTIFICATION BRACELET

TECHNICAL FIELD

Embodiments disclosed herein relate generally to the field of identification devices, and more particularly to wearable identification bracelets.

BACKGROUND ART

Wearable identification bracelets are used to alert others of medical conditions and personal data. These medical emergency bracelets also known as Med-Alert bracelets contain information engraved into the bracelet, which is typically a metallic band worn around a user's wrist. Such information can be a combination of personal and medical data. However, these bracelets contain information that cannot be easily customizable or changed overtime and often any change in the data necessitates a whole new bracelet replacement. The bracelets do not allow the caregiver or wearer to personally create information that can be stored and accessible via the bracelet. Moreover, these known bracelets are often not waterproof and not suitable for storing and displaying extensive personal and medical information data. Additionally, these bracelets are not comfortable to wear.

Therefore, there is a need for a wearable waterproof identification bracelet that is comfortable to wear and that is configured to inform, alert and empower end-users and to store extensive medical and personal data in printed and electronic format, which can be easily changed or customized overtime.

SUMMARY OF THE EMBODIMENTS

The present invention provides a wearable identification bracelet. The identification bracelet includes a wristband securable to a wearer. The wristband includes a plurality of openings for receiving a locking rivet and one or more openings for receiving one or more color-coded pins, a housing attached to the wristband, the housing having a pair of lugs with a slit, each lug extending from each side of the housing and adapted to receive the corresponding ends of the wristband inserted into the corresponding slits. The housing comprises a snap-on cover with at least a portion of the cover being transparent, a base, and a waterproof gasket insertable into the base. The snap-on cover is configured to be snapped on the base thereby creating a hermetically sealed waterproof structure. The housing also includes an information tag insertable into the housing and visible through the transparent portion of the housing. In some instances, the color of one or more color-coded pins corresponds to an alert or a medical condition of the bracelet wearer.

The information tag can be a printed label with a bar code. The identification bracelet can further include an RFID or NFC chip. It can also include a separation pad for separating the information tag from the RFID or NFC chip. The information tag can be an NFC or RFID tag. The information tag can include personal, medical, emergency or their combination information about the wearer of the bracelet. In some instances the information tag can include information related to evacuation of residents in accordance with transportation assistance levels (TALS) guidance.

Other aspects, embodiments and features of the device and method will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the device and method shown where illustration is not necessary to allow those of ordinary skill in the art to understand the device and method.

BRIEF DESCRIPTION OF THE DRAWINGS

The preceding summary, as well as the following detailed description of the disclosed device and method, will be better understood when read in conjunction with the attached drawings. It should be understood, however, that neither the device nor the method is limited to the precise arrangements and instrumentalities shown.

DETAILED DESCRIPTION OF SPECIFIC EMBODIMENTS

The present disclosure provides a wearable waterproof identification bracelet that can be worn by a user and is configured to inform, alert and empower end-users and to store extensive medical and personal data, which can be easily changed or customized overtime.

Figure 1:
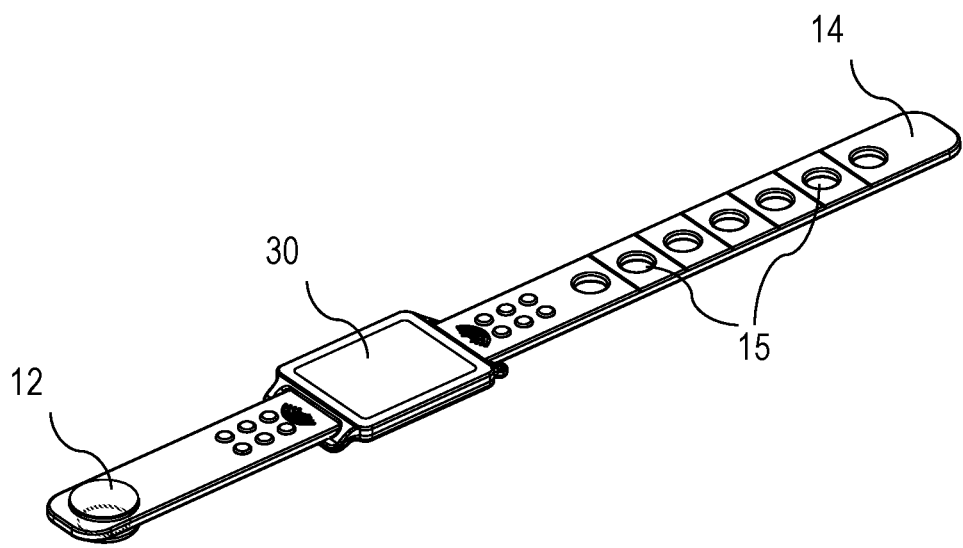
FIG. 1 is a front perspective view of a disclosed identification bracelet in the assembled state embodying the invention.
Figure 2:
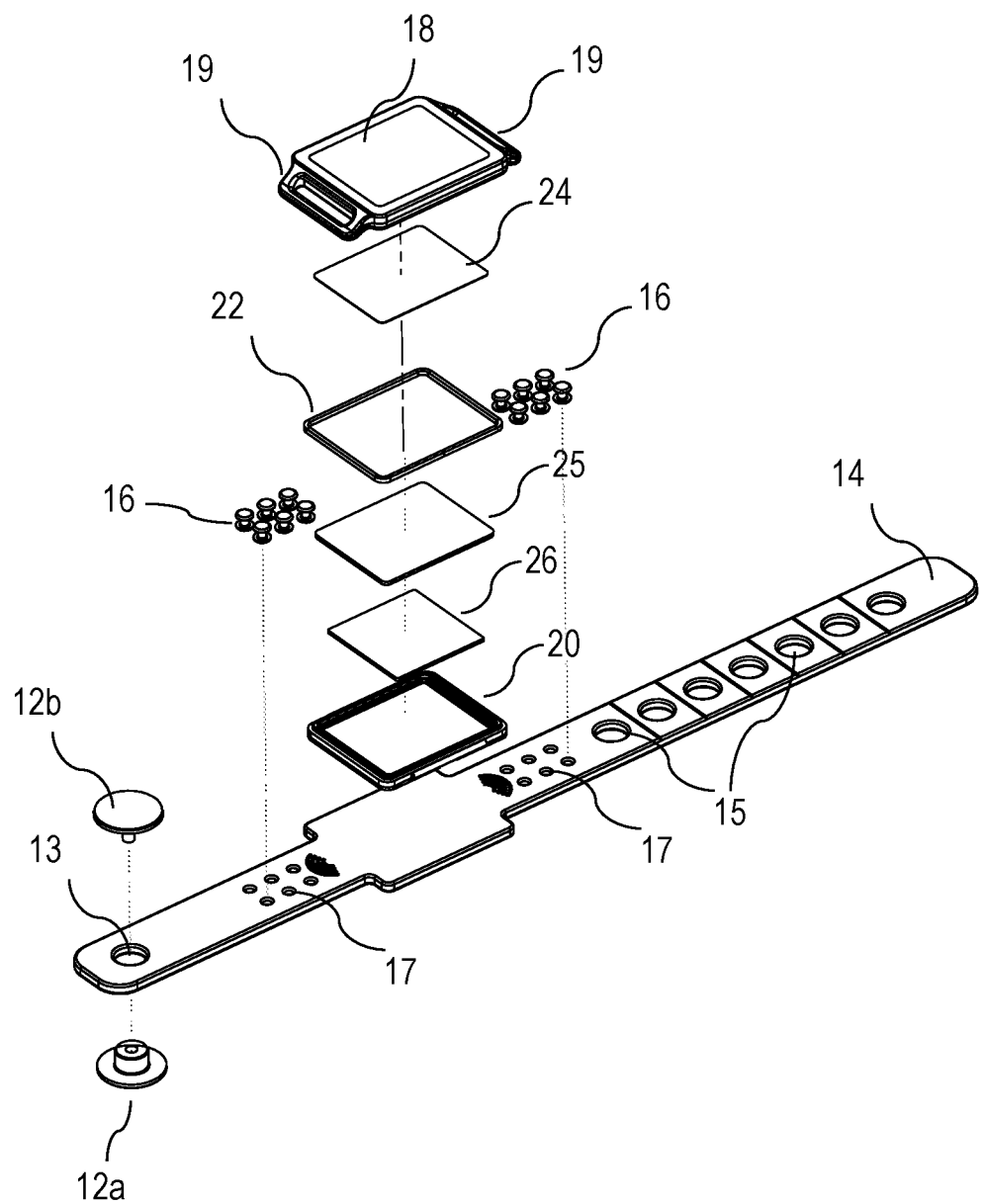
FIG. 2 is perspective view of a disclosed identification bracelet in the disassembled state.

Referring now to the drawings in detail, and particularly to FIG. 1, there is shown a front perspective view of a disclosed identification bracelet in the assembled state embodying the invention. The bracelet 10 includes a housing 30 releasably coupled to an adjustable wristband 14 having a locking rivet 12 and opening 13 on one side of the wristband and one or more corresponding openings 15 on the other side of the wristband for receiving the locking rivet 12 thereby securing the wristband on a wrist of a user. As shown in FIG. 2, the locking rivet 12 consists a female component 12*a* and male component 12*b* which are designed to simply snap together with finger pressure and provide a neat appearance on both sides of the wristband 14. Once assembled, the locking rivet 12 is difficult to remove and must be cut off from the wristband. The rivet can be made of polycarbonate clear or nylon black materials, or any other suitable materials. The wristband 14 can also include one or more openings 17 for receiving one or more color-coded pins 16, which can carry some essential information about a patient in a hospital or a nursing home, for example. The wristband 14 is adjustable to fit the wearer and can be made of any suitable materials for the intended uses of the device. Exemplary materials include plastics such as PVC, elastomer, silicon, polyethylene, nylon, polymer; or fabrics, leather, and combinations thereof. The choice of materials is reflected in preferred qualities of the wristband such as flexibility, having no sharp edges, no irritation of skin, breathability and long-term reliability, especially when immersed in water. The wristband may be formed from a single piece of material or a combination of different pieces. It will be readily appreciated by a person skilled in the art that band 14 can be applied not only to a wrist of a wearer but also to some other limbs, around an ankle, for example, or can be worn around an upper arm of a user. It will be appreciated by a person skilled in the art that some other alternative locking/securing means can be utilized in order to secure the wristband around a wrist of a user. For example, a conventional locking mechanism used in wristwatch bands can be employed; such as a combination of other side of the wristband. It should be noted that the advantage achieved by utilizing color-coded pins in accordance with the present disclosure is that pins are readily viewed by medical staff from a distance and that pins can be easily changes as the patient's condition changes as opposed to the current state of the art where information is printed on the band and is not visible or easily changed without fabricating a new band altogether. In some instances, instead of pins, other color-coded indicators could be used for the purpose such as buttons, flags, rings, links, or stripes attached with various suitable attaching means such as adhesives, for example.

TABLE 1

| Message | Purple | Blue | Teal | Green | Red | Pink | Orange | Yellow | White |
|---|---|---|---|---|---|---|---|---|---|
| DNR | v | v | | | v | v | | v | |
| Limited DNR | | | v | | | | | | |
| Fall Risk | v | v | | v | v | v | v | v | v |
| Restricted Extremity | v | v | | v | v | v | v | v | v |
| Allergy (no latex) | v | v | | v | v | v | v | v | |
| Allergy to Latex | v | v | | v | | | | | |
| Tape Allergy | | v | | | | | | | |
| Procedure Site | v | | | | | | | v | v |
| Blood Type/Bank | | | | v | v | v | | | |
| No Blood Products | | | | | | | v | | |
| Outpatient or ER | | v | | v | | v | v | v | |
| Pediatrics/Mother-Child Match | | | | | | | | v | v |
| Parent/Guardian | | v | | | | | | | |
| Similar Name | | v | | | | | | | |
| Observation | | | | | | | v | | |
| Isolation | | | | v | | | | v | |
| Elopement | | v | | | | | | | |
| Pacemaker | | v | | | | | | | |
| Anticoagulants | | v | | | | | | | |
| NBM | | | | | | | | v | |
| Dietary Restrictions | v | | | | | | | | |
| Diabetics | | v | | | | | | | | adjustment holes on one side of the band and tang buckle and free loop/keepers on the other side of the band, or a clasp mechanism.

Figure 5:
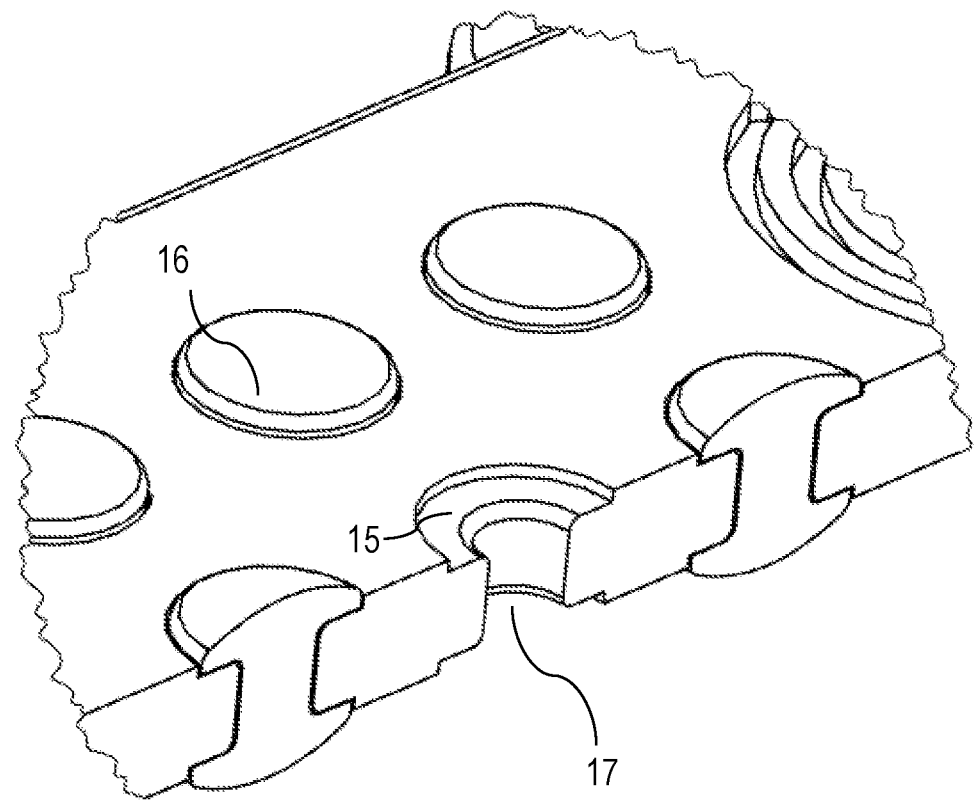
FIG. 5 is a schematic cross-sectional view of a tamper-proof recessed color-coded pin configuration.

In some instances, as illustrated in FIG. 5, as a tamper-proof solution, color-coded pins 16 can be inserted into corresponding openings 17 having recessed areas 15 such that the heads of the color-coded pins are partially submerged into openings thereby making it difficult for a wearer of the bracelet to remove the pins by getting fingernails under the heads of the pins to pull.

Figure 3:
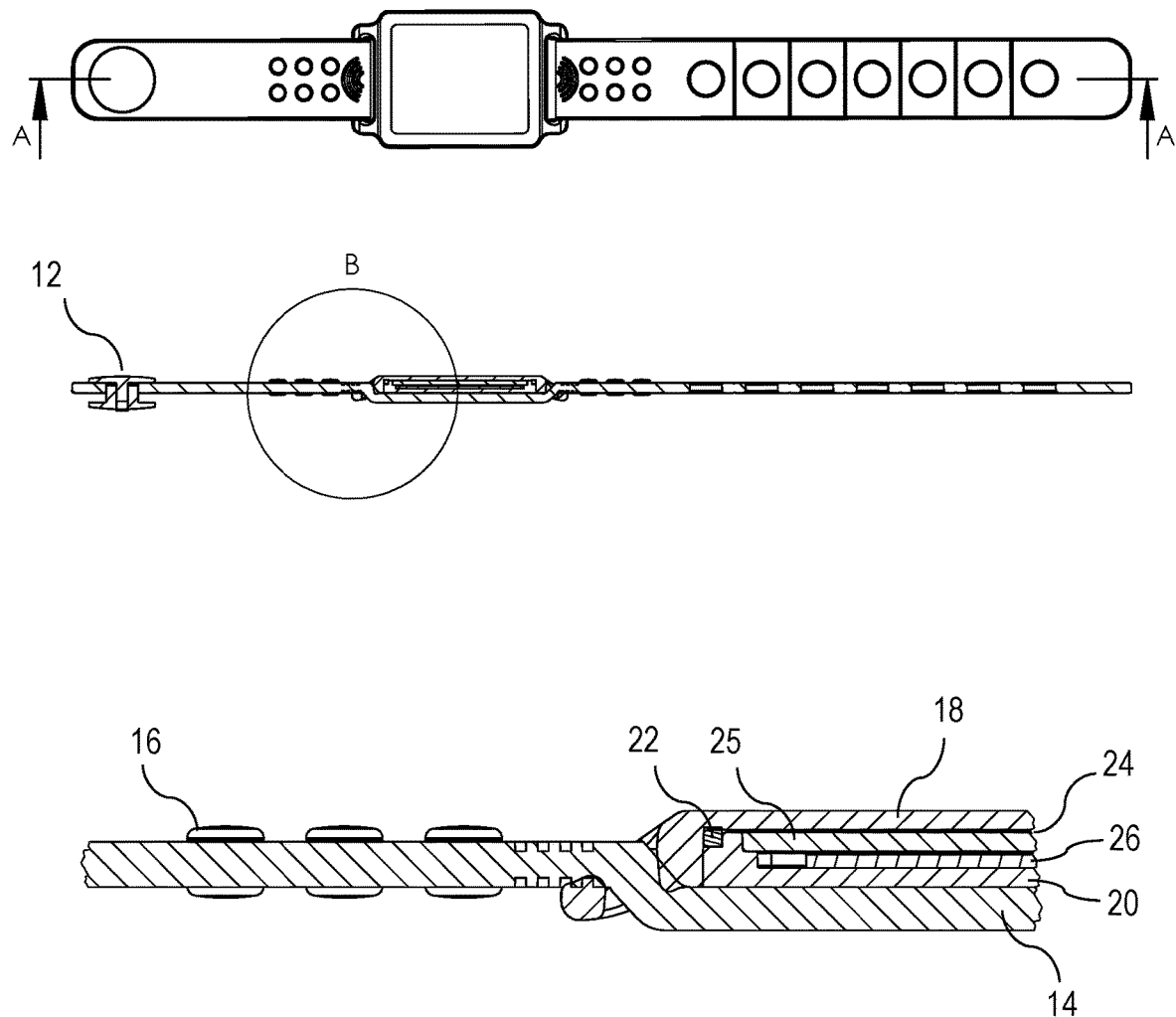
FIG. 3 is a top view of a disclosed identification bracelet showing a cross-sectional view along the line A-A and a cross-sectional view of a magnified portion B.
Figure 4:
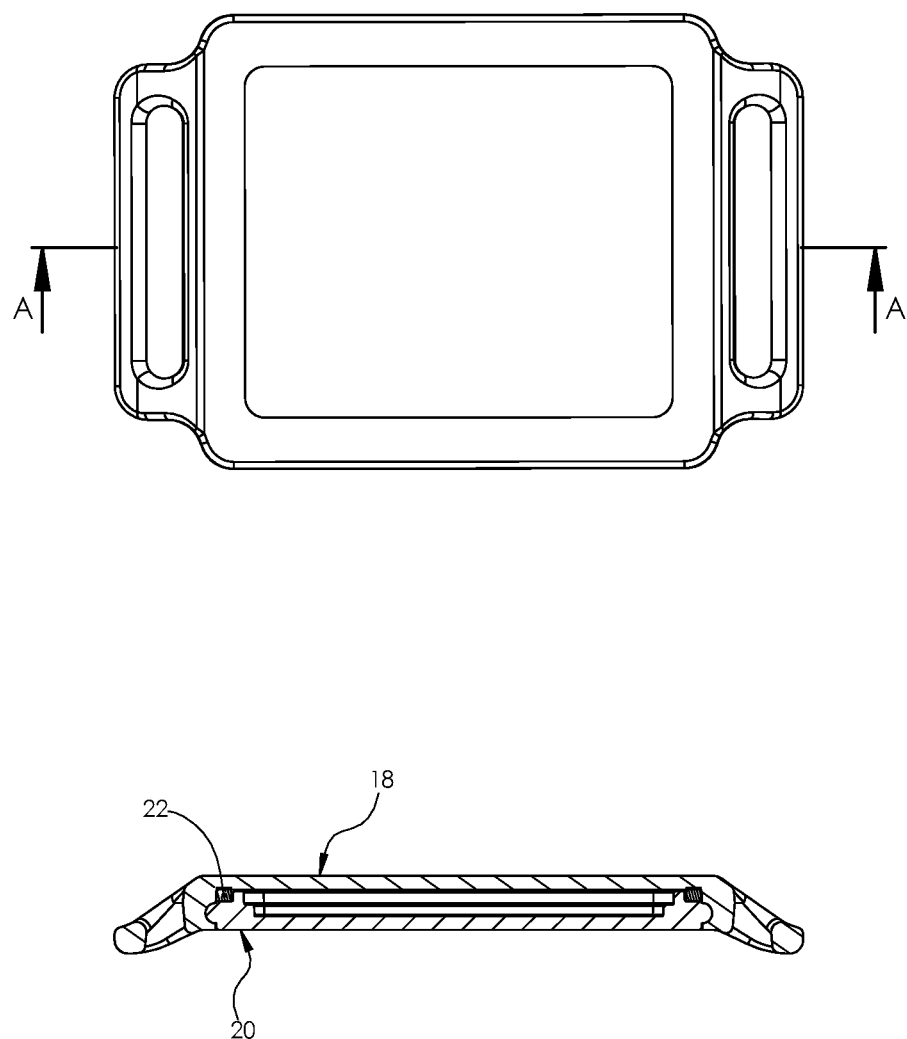
FIG. 4 is a top view of a disclosed identification bracelet showing a housing with a gasket without a wristband and a cross-sectional view along the line A-A.

Table 1 shows a typical application of colors in hospitals and/or nursing homes created by the Pennsylvania Patient Safety Authority. Each color of a color-coded pin can be assigned to a particular alert or medical condition. For example, a green pin can signify that a patient is prone to allergy to latex and blue pin to fall risk, while a purple pin could carry indicia of dietary restrictions. According to a preferred embodiment of the present disclosure, there can be six color-coded pins 16 disposed on each side of the wristband, inserted into corresponding openings 17 as shown in FIG. 2. In some instances, there could be three color-coded pins on each side of the wristband. In some embodiments, only one color-coded pin is disposed on each side of the wristband. A person skilled in the art would readily understand that there could be any suitable number of pins on each side of the wristband. In some instances, there could be one or more pins on one side of the wristband and no pins on the The waterproof housing 30 is releasably attached to wristband 14 and is adapted to hermetically store one or more identification labels and/or tags. The housing 30 includes a snap-on cover 18 having a pair of lugs 19 extending from the cover 18 for receiving the wristband 14 adapted to be inserted into slits of lugs 19 as shown in FIG. 2. It can be appreciated by a person skilled in the art that the slits of lugs 19 can alternatively be formed by a pair of corresponding spring bars inserted into the lugs extending from the cover, similar to attaching means of conventional watches. The cover 18 is configured to be snapped on base 20 thereby creating a hermetically sealed waterproof housing for storing one or more identification tags. A waterproof gasket 22 is disposed in the base 20 for creating a tight waterproof seal, as shown in FIGS. 3-4. At least some portion of the cover 18 is clear such that an identification tag placed inside the housing 30 can be partially or entirely visible. The housing 30 can include an identification tag in the form of a label 24 having a bar code for scanning. The label 24 is sized to fit within the housing. The label 24 can include some initial information about a user, such as a small picture, user's name, room number and a barcode with a medical record number (MRN). The label 24 can be water-resistant and/or waterproof. In some instances it can be a piece of paper or another type of material, such as, for example, plastic or the like. In some instances of the present disclosure, instead or in addition to the label 24, an identification tag can include an RFID tag or NFC chip 26 as shown in FIG. 2. The housing 30 can also include a separation pad 25 for separating bar-coded label 24 and RFID/NFC tag 26. The information stored on the label 24 can be accessible by means of a bar-code reader that may be scanned to obtain information on the user from a database. The information may be downloadable using Radio Frequency Identification (RFID) or Near Field Communication (NFC) technologies if the NFC and/or RFID tag 26 is used. It will be appreciated by a person skilled in the art that the information can be stored in some other forms, such as magnetically (magnetic swipe) or in a memory chip or flash memory or other forms of data storage. In some instances, a hybrid chip integrating both the RFID and NFC technologies could be utilized.

The described-above embodiments of the identification bracelet of the present disclosure can be utilized in various applications. The bracelet can be used in a nursing home setting, taking advantage of the richness of the data that can be stored and the ease of access to that data. For example, the bracelets can store food preferences or names and phone numbers of family members for nurses to use, the options which were not previously available on commercially available prior art wrist band devices. Another advantage of the presently disclosed identification bracelets is that they can be updated all at once (en mass) without having to reprint all the bands. Another application of the presently disclosed identification bracelets is for the purpose of an evacuation of patients/residents in accordance with transportation assistance levels (TALS) guidance. The TAL classifications are as follows.

TAL-1: Non-ambulatory. This rating is meant for patients who are bedbound and unable to sit upright for long periods of time. In the event of an emergency, the city 911 system will dispatch FDNY and EMS staff to assist the client by stretcher into an ambulance for transportation.

TAL-2: Wheelchair. This rating indicates that a client is unable to walk short distances due to a physical or medical condition. When an evacuation occurs, paratransit services like Access-A-Ride are used to transport patients to safety.

TAL-3: Ambulatory. This final rating is reserved for patients who can safely walk without the assistance of others and includes patients who use a cane, walker or similar device. When an evacuation occurs, paratransit services like Access-A-Ride.

The TAL workflow can be described as follows. During Emergencies Staff and EMS Staff need to know critical information is needed to Transport patient safely. The TAL application and Web Service has been developed to provide a way to maintain the TAL data directly with the patient. The Bracelet has the ability to contain 1 k of information. The data is captured using the Facility EMR or a Smartphone Application and transferred to a Cloud Service. In some instances, the data can comprise geo-coordinates to track the location of a patient wearing a bracelet, which was scanned by a mobile device such as a smart phone containing a GPS chip. The data can be held in a HIPAA secured cloud service. Because the data on the bracelet is also stored in a secured cloud service, it allows a user, once the bracelet is scanned, to have access to more information critical to caring for patients, which greatly enhances the functions of the bracelet of the present disclosure, especially for medical alert bracelet applications.

Admission Patient Bracelet. Patient Label and Barcode are printed and inserted into the Bracelet Base. Waterproof cover is placed over the Label and Base. Patient Reference Number is written to the NFC Chip. Bracelet is placed on the Patient/Resident.

TAL Assessment. TAL Data is collected via an EMR Assessment Program or the TAL App. EMR Transmits the Assessment and Score to the TAL Cloud Service via API Call. TAL App allows the user to enter the data using the Smartphone and write the information to the bracelet.

Updating the Bracelet. Using a Smartphone User selects the Patient by Scanning Bracelet or Entering the Patient Id. TAL Update App loads the Associated information to the Smartphone. Smartphone is placed in the Primed Mode. Smartphone is placed over the Chip and Writes the TAL Data to the NFC/RFID chip in the Bracelet. As mentioned above, in some instances, the data can comprise geo-coordinates to track the location of a patient wearing a bracelet. Once the bar code and/or NFC chip is read/scanned using a mobile device containing a GPS chip, the geo-coordinates of a scan are stored in a database located in the cloud service, for example. In some instances, the geo-coordinates data can be stored locally on a mobile device, for example. Accessing the geo-coordinates data, a user of the presently disclosed system can determine a location of a bracelet wearer at a particular point in time.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

The foregoing detailed description is merely exemplary in nature and is not intended to limit the invention or application and uses of the invention. Furthermore, there is no intention to be bound by any expressed or implied theory presented in the preceding technical field, background, brief summary, or the following detailed description.

What is claimed is:

1. A wearable identification bracelet comprising:
    a wristband securable to a wearer, the wristband having a plurality of openings for receiving a locking rivet and one or more openings for receiving one or more color-coded pins;

a housing attached to the wristband; wherein the housing comprises a snap-on cover with at least a portion of the snap-on cover being transparent, a base, and a waterproof gasket insertable into the base; wherein the snap-on cover having a pair of lugs with a slit, each lug extending from each side of the snap-on cover and adapted to receive the corresponding ends of the wristband inserted into the corresponding slits; wherein the snap-on cover detachably coupled to the base is configured to be snapped on the base thereby creating a hermetically sealed waterproof structure; and an information tag insertable into the housing and visible through the transparent portion of the housing; wherein the color of one or more color-coded pins corresponds to an alert or a medical condition of the bracelet; wearer wherein the one or more color-coded pins terminate in a round head at each end of the pin.

2. The bracelet of claim 1, wherein the information tag is a label having a bar code.

3. The bracelet of claim 2, wherein the label comprises printed information about the wearer of the bracelet selected from the group consisting of personal, medical, emergency information, or combination thereof.

4. The bracelet of claim 1, further comprising an RFID tag.

5. The bracelet of claim 4, further comprising a separation pad adapted to separate the information tag from the RFID tag.

6. The bracelet of claim 4, wherein the RFID tag comprises personal, medical, emergency, or combination thereof information about the wearer of the bracelet.

7. The bracelet of claim 6, wherein the emergency information comprises evacuation of residents in accordance with transportation assistance levels (TALS) guidance.

8. The bracelet of claim 1, further comprising an NFC chip.

9. The bracelet of claim 8, further comprising a separation pad adapted to separate an information tag from the NFC chip.

10. The bracelet of claim 8, wherein the NFC chip comprises personal, medical, emergency, or combination thereof information about the wearer of the bracelet.

11. The bracelet of claim 10, wherein the emergency information comprises evacuation of residents in accordance with transpiration assistance levels (TALS) guidance.

12. The bracelet of claim 1, wherein the information tag comprises an RFID tag, or an NFC chip, or both.

13. The bracelet of claim 1, wherein the locking rivet comprises a male component adapted to be inserted into a female component for securing the band around a wrist of a wearer.

14. The bracelet of claim 1, wherein the information tag is water-resistant or water proof.

15. The bracelet of claim 1, wherein each of the one or more openings for receiving the one or more color-coded pins includes a recessed area such that the round head of each color-coded pin is partially submerged into a corresponding opening of the one or more openings.

16. A method of assembling a wearable identification bracelet, comprising:
   printing a label with a bar code comprising information about a user;
   inserting a waterproof gasket into a base of a housing;
   inserting the printed label into the base of the housing;
   detachably snapping a snap-on cover having at least a portion of the cover being transparent onto the base of the housing thereby creating a hermetically sealed waterproof structure; wherein the snap-on cover having a pair of lugs with a slit, each lug extending from each side of the snap-on cover and adapted to receive the corresponding ends of a wristband inserted into the corresponding slits; wherein the printed label is visible through the transparent portion of the snap-on cover;
   inserting one or more color-coded pins terminating in a round head at each end of the pin into one or more corresponding openings in the wristband;
   releasably attaching the wristband to the housing; and
   securing the wristband around a wrist of a user with a locking rivet.

17. The method of claim 16 further comprising inserting an RFID or NFC chip or both into the base.

18. The method of claim 17 further comprising inserting a separation pad between the label and the RFID or the NFC chip.

19. A kit comprising:
   a wristband securable to a wearer, the wristband having a plurality of openings for receiving a locking rivet and one or more openings for receiving one or more color-coded pins terminating in a round head at each end of the pin;
   a housing releasably attached to the wristband; wherein the housing comprises a snap-on cover with at least a portion of the cover being transparent, a base, and a waterproof gasket insertable into the base; wherein the snap-on cover having a pair of lugs with a slit, each lug extending from each side of the snap-on cover and adapted to receive the corresponding ends of the wristband inserted into the corresponding slits; wherein the snap-on cover detachably coupled to the base is configured to be snapped on the base thereby creating a hermetically sealed waterproof structure; and
   an information tag, wherein the information tag is configured to be printed with information about a wearer of the identification bracelet; and is visible through the transparent portion of the snap-on cover.

20. The kit of claim 19, wherein the information tag further comprising a bar code.

21. The kit of claim 19, further comprising an RFID tag or an NFC chip.

* * * * *